US006639670B2

(12) United States Patent
Carpenter

(10) Patent No.: US 6,639,670 B2
(45) Date of Patent: Oct. 28, 2003

(54) CALIBRATION TOOL FOR LASER PARTICLE COUNTERS

(75) Inventor: Steven E Carpenter, Philomath, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 105 days.

(21) Appl. No.: 09/966,305

(22) Filed: Dec. 18, 2001

(65) Prior Publication Data

US 2003/0112434 A1 Jun. 19, 2003

(51) Int. Cl.[7] .............................................. G01N 15/02

(52) U.S. Cl. ..................................................... 356/335

(58) Field of Search ................................ 356/335, 336, 356/337, 338, 339, 340, 341, 342, 343, 438, 439; 437/40, 74, 75, 81; 250/574; 702/26; 239/1

(56) References Cited

U.S. PATENT DOCUMENTS 5,296,910 A * 3/1994 Cole ......................... 356/28.5
5,796,480 A * 8/1998 Igushi ........................ 356/336
6,111,642 A 8/2000 DeFreez et al. ............ 356/337
6,126,086 A 10/2000 Browner et al. ......... 239/102.1

OTHER PUBLICATIONS

"Aerosol Particle Generator", Model 255, Met One, Inc.

"Liquid Particle Counting Systems for In–Situ Sampling", Particle Measuring Systems Inc., 1991.

"Liquid Particle Counting Systems for Volumetric Sampling", Particle Measuring Systems Inc., 1991.

D.F. Parsons, "A multitasking particle characterization system for laboratory and process control", American Laboratory, pp. 29–33, (Jul. 1992).

D.F. Nicoli et al., "Automatic, high–resolution particle size analysis", American Laboratory, pp. 39–44, (Jul. 1992).

H.T. Sommer et al., "Beyond Class 1 Clean Rooms: Particle Contamination Detection in Ultra Clean Environments", pp. 1–8.

Hwa–Chi Wang et al., "Counting particles in high–pressure electronic specialty gases", Contamination Control, (Jun. 1994) Solid State Technology, pp. 97–107.

H.T. Sommer et al., "Examining molecular background scattering and the trade–off between sensitivity and sample flow rate of optical particle counters", Microcontamination (Mar. 1991), pp. 35–64.

D.F. Nicoli et al., "Application of Dynamic light scattering to particle size analysis of macromolecules", (Nov. 1991) American Laboratory, pp. 32–38.

E.M. Johnson et al., "An automated CNC based filter tester for fast penetration testing of HEPA and ULPA media", Solid State Technology, (Sep. 1990), pp. 113–118.

R.G Knollenberg et al., "The measurement of particle sizes below 0.1 micrometers", pp. 1–10.

R.G. Knollenberg et al., "Optical particle monitors, counters and spectrometers: performance characterization, comparison and use", pp. 1–20.

W.W. Szymanski et al., "On the sizing accuracy of laser optical particle counters", (1986), pp. 1–7, VCH Verlagsgesellschaft mbH; 0176–2265/86/0104–0001.

(List continued on next page.)

*Primary Examiner*—Alan A. Mathews

(57) ABSTRACT

A calibration system for a particle counter comprising a chamber, an air inlet pathway and a supply source of a liquid carrier. The air inlet pathway provides a gaseous substance into the chamber, and the liquid carrier passes through an array of thermal inkjet heads with a plurality of orifices to form a plurality of liquid particles before the liquid particles are entrained by a flow of the gaseous substance. A controller regulates the size, amount, and rate of liquid particles that exit the array.

21 Claims, 4 Drawing Sheets

OTHER PUBLICATIONS

Jin Jwng Wu et al., "Process Improvement using in–situ particle detection", Journal of the IES, May/Jun. 1993, pp. 21–24.

C.A. Pashby et al., "Guidelines for Selecting an Optical Particle Counter", pp. 3–1.3–1.11, (Apr. 1991), Met One, Inc.

"Precision Component Cleaning: Using the Model 211W Liquid–Borne particle sensor for solvents and cleaning fluids", Met One Outlook (Jul. 1989), pp. 1–4.

Hewlett Packard Met One Quotation SYS0693–00–A, Mar. 17, 1993, Summary Sheet, pp 2–10.

"Multi–Port Technology Reduces Cost of Monitoring Multiple Locatrions", Particle Counter Talk, Met One update on Particle Counting Technology, Fall/Winter 1992, pp. 1–4.

Met One, "Model 205 Laser Based Airborne Particle Counter and Environmental Monitor".

Met One, "Model 200L Clean Room Monitor".

Met One, "Model 209D Laser Based Airborne Particle Counter and Environmental Monitor".

Met One, Your Greatest Liquid Assets, "Met One Liquid particle Monitoring Systems", Model 210 Liquid Particle Counting System, Model 233 Dual Sensor Liquid Particle Counting System, Model 250 Automatic Batch Sampling System, Model 203 Facility Particle Counting System, Model 211W Liquid Laser Sensor (NEMA).

Met One, Owners Manual, "Model 217 Laser Particle Counter", (Jul. 1990) Met One, Inc.

Met One, "M2000 Software Operating Guide for the A2020, A2090, A2300, and A2320 Particle Counters", (Oct. 1992), Met One, Inc.

Met One, "Particle Counters For Air, Application and Maintenance", (1992), Met One, Inc.

* cited by examiner

CALIBRATION TOOL FOR LASER PARTICLE COUNTERS

FIELD OF THE INVENTION

The present invention relates generally to calibration systems. More particularly, the present invention relates to a calibration tool for a laser air particle counter.

BACKGROUND OF THE INVENTION

Laser air particle counters are currently used in a variety of industries. For example, many optical particle counters are used for monitoring a level of contamination in clean room facilities.

Many types of particle counters include a laser beam which, when coming into contact with an air particle, sends a signal to a tabulation device which keeps track of the number of particles that are registered during a given amount of time. Several particle counters also include methods of not only counting the number of particles that pass through a laser beam, but also registering the size of individual particles and the density of particles in varying locations of a room. Such devices are particularly important in clean rooms where highly sensitive equipment is being manufactured. Additionally, particle counters can be heavily relied upon in hospital operating rooms or medical facilities where biotechnological innovations are being investigated and developed. In such locations, it is extraordinarily important that the particle counters operate as accurately and precisely as possible; even a slight degree of error in the particle counter could result in massive contamination. This can cause a product of manufacture to contain undesirable defects and, in the case of a hospital operating room, can result in an increased amount of infection and medical complications for patients.

Additionally, even highly accurate and precise particle counters often need to be checked and calibrated to ensure that the particle counters maintain a high degree of reliability. Furthermore, particle counters need to be checked on a regular basis to determine whether or not the counter needs to be replaced.

For the above reasons, entities that manufacture and use particle counters also use calibration systems to monitor the accuracy and preciseness of their particle counters. Calibration systems are operatively connected to the particle counter and release particles of a known size and at a known rate into the particle counter. The particle counter proceeds to count the number and size of these particles and this number is compared to a size and number of particles that were released according to the calibration system. If there is a difference between the two devices that is outside of an acceptable error range, the user is able to determine whether it is necessary to repair and/or replace the particular counter.

One common type of calibration system includes one or more chamber of polystyrene latex spheres (PLSs). In each chamber all of the polystyrene spheres have a known size. When calibration is desired, the calibration system is coupled to the particle counter, and the polystyrene latex spheres are released from one of the chambers at a known rate. A nebulizer entrains the polystyrene spheres into a fine spray, and the polystyrene latex spheres are counted by the particle counter. The size and number of particles that are recorded by the particle counter are then compared to the known quantities from the calibration system.

Although such calibration systems are useful, they also include a number of drawbacks. For example, polystyrene latex spheres must often be purchased separately from a third party. Furthermore, polystyrene spheres of different sizes must also be purchased and often stored separately. Additionally, such calibration systems that include multiple chambers of polystyrene spheres can become relatively large and cumbersome. The systems may also require frequent and repetitive cleaning after a certain number of uses. Finally, nebulizers used with such calibration systems are often relatively expensive to manufacture and/or purchase.

SUMMARY OF THE INVENTION

The present invention provides for a calibration tool utilizing thermal inkjet printing technology. A closed chamber includes an inlet for receiving clean air or another gaseous substance and an outlet that is operatively connected to the chamber. A solution of a liquid carrier is coupled to the chamber, and the chamber also includes an array of thermal inkjet heads with each head including different sized orifice plate openings. The liquid carrier passes through the array of thermal inkjet heads and combines with the air entering the chamber to form a fine spray. A controller regulates the rate at which individual particles pass through the array and also regulates whether certain orifice plate openings are opened or closed.

Another aspect of the invention provides for a particle counter calibration system comprising a calibration chamber including an air intake portion for transferring a stream of a gaseous substance, and an array of inkjet heads including a plurality of orifices of different sizes. A supply of a liquid carrier is operatively connected to the chamber, and a control unit is operatively connected to the array of plates and the supply of liquid carrier. The liquid carrier passes through the array to form a plurality of liquid particles flowing through the chamber, and the size of the liquid particles and the rate at which particles exit the array are regulated by the control unit.

Another aspect of the invention provides for a system for calibrating a particle counter comprising an inlet passageway for receiving a gaseous material. A chamber is operatively connected to the air inlet passageway and includes an array of inkjet heads having orifices of different sizes. A reservoir supplies a liquid material to the chamber. A particle counter is operatively connected to the chamber, and means for controlling the number of liquid particles that exit the array are coupled to the chamber. When the liquid material is combined with the gaseous substance, a plurality of liquid particles is formed and flows through the chamber. The controlling means regulates the size of the particles and the rate at which the particles exit the array and enter the particle counter.

The present invention allows for the use of thermal inkjet droplets which are much less expensive than polystyrene latex spheres while also permitting the calibration tool to be smaller in size and also reducing the need for regular cleaning of the equipment.

DETAILED DESCRIPTION OF THE PREFERRED EMBODIMENTS

Figure 1:
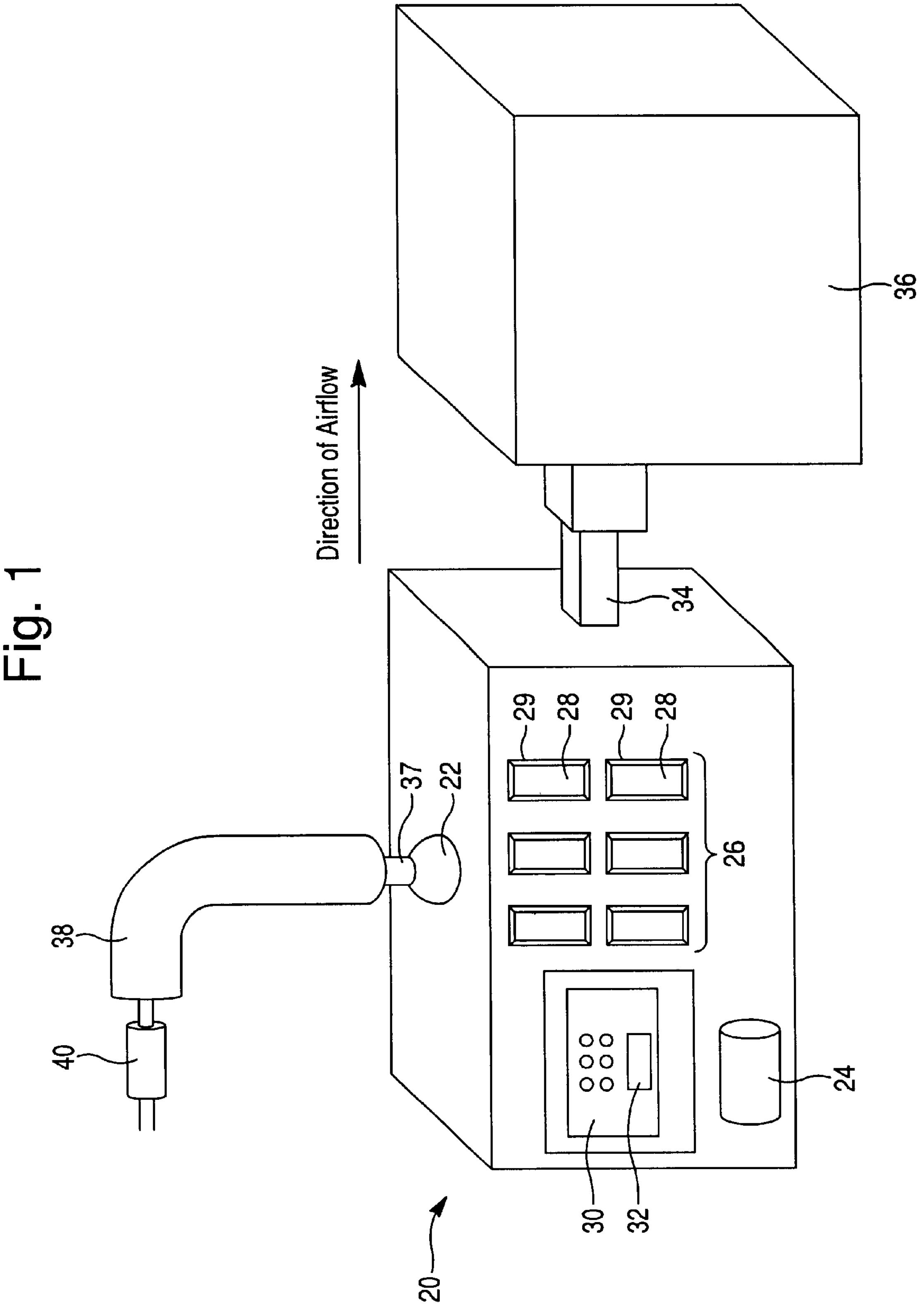
FIG. 1 is a representation of a thermal inkjet calibration tool and a standard particle counter in accordance with the present invention.

FIG. 1 is a representation of a thermal ink jet calibration system in accordance with one embodiment of the present invention. A ink jet calibration tool, shown generally at 20, includes an air intake port 22, a solution supply source 24, and a thermal ink jet array 26. The thermal ink jet array 26 includes a plurality of orifice plates 28 on individual calibration heads 29, as will be discussed later. The ink jet calibration tool 20 also includes a control unit 30 having a display unit 32, although the display unit 32 may also be included separately.

The air intake port 22 may be operatively coupled via a connector 37 to a tubing 38. Both the type and length of the tubing 38 may vary depending upon the particular system requirements. The tubing 38 may be coupled at the opposite end to an air filter 40. Depending upon the particular system requirements, the air filter 40 may be a standard, commercially available air filter. The air filter 40 is coupled to a commercial blower (not shown) or a comparable system for providing a stream of air or other gaseous substance to the ink jet calibration tool 20. In one embodiment of the invention, standard atmospheric air is filtered and used in the ink jet calibration tool 20, although it is possible that other gaseous substances could be used without departing from the invention's broader aspects.

Figure 5:
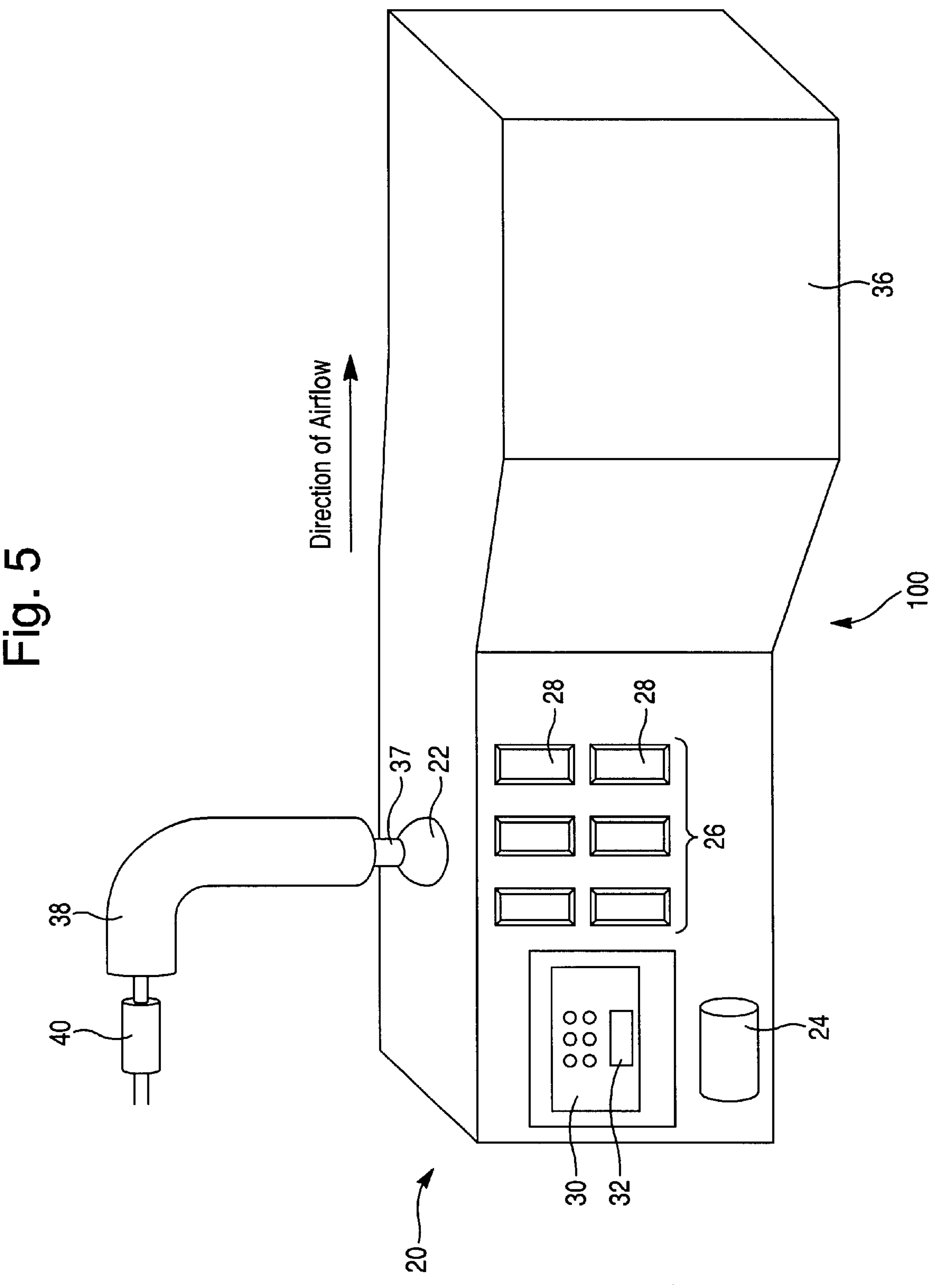
FIG. 5 is a combined ink jet calibration tool and particle detector according to another embodiment of the invention.

The ink jet calibration tool 20 can be directly coupled to a particle counter 36 such a laser air particle counter with an intake pump. In one embodiment of the invention, the particle counter 36 is coupled to the ink jet calibration tool by an exit tube 34. Alternatively, it is also possible for the calibration tool 20 and the particle counter 36 to be integrated into a single unit, shown as 100 in FIG. 5. The exit tube 34 is a simple air connector in one embodiment of the invention, and the exit tube can be of virtually any length and/or diameter depending upon the particular particle counter 36 that is to be used.

The solution supply source 24 can either be integrated directly into the ink jet calibration tool 20 or be included as a remote component which is operatively connected to the ink jet calibration tool 20. In one embodiment of the invention, the solution supply source 24 includes a standard ink jet printing ink as used in pen bodies manufactured by Hewlett Packard. It is also possible, however, that other types of ink can be placed in the solution supply source 24. Additionally, it is possible that materials other than ink can be used in the ink jet calibration tool 20.

Figure 2:
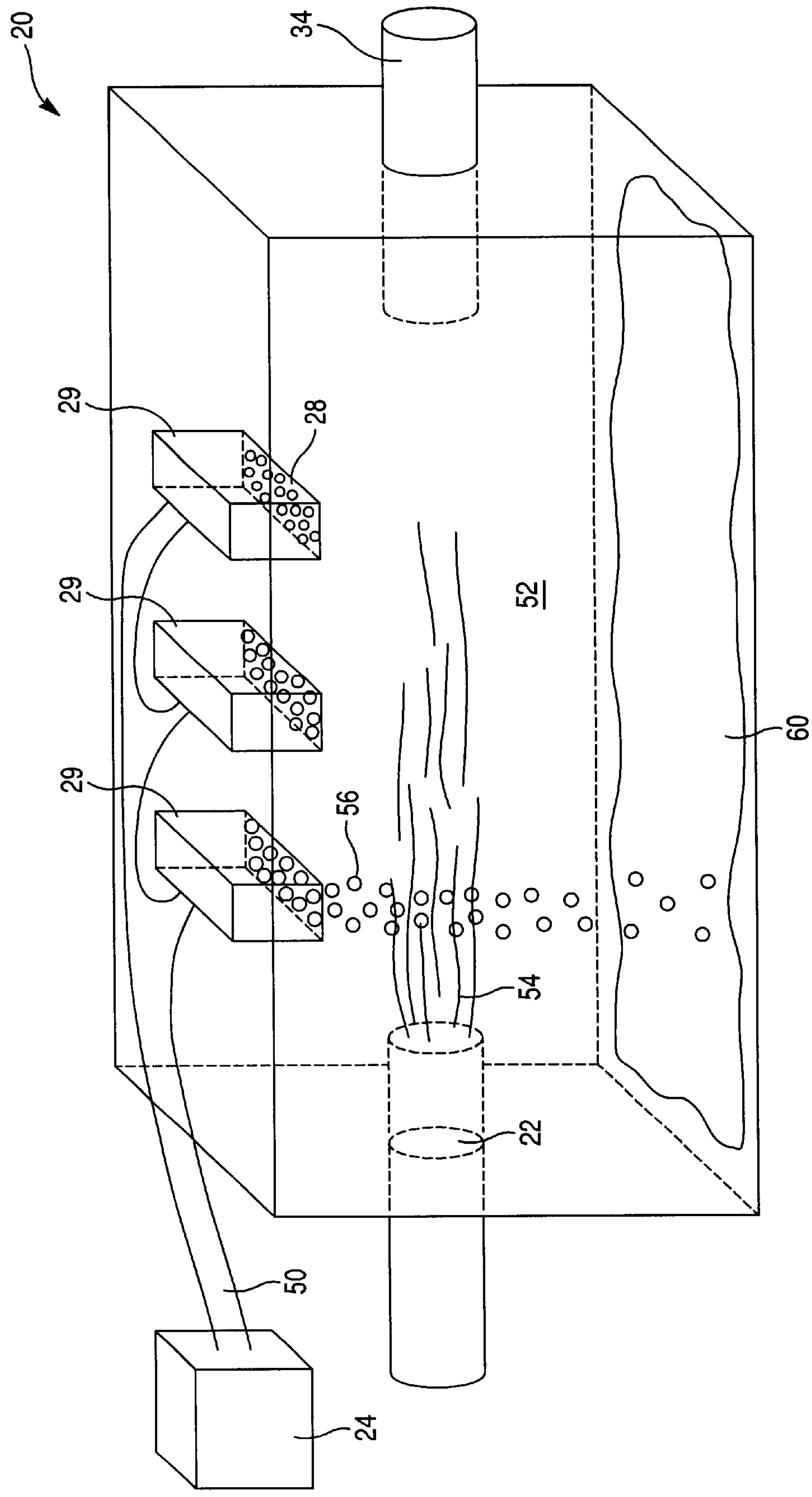
FIG. 2 is a representation of the internal structure of an alternative calibration tool.

FIG. 2 shows the general internal structure of one embodiment of an ink jet calibration tool 20. In this particular embodiment of the invention, the solution supply source 24 is located remotely from the ink jet calibration tool 20 and is coupled thereto by a connecting conduit 50. Additionally, the ink jet array 26, as shown in FIG. 1, is located at the top of the ink jet calibration tool 20 rather than at the side thereof. Other positions for these individual components and others are also possible.

The ink jet calibration tool 20 includes a central chamber 52 in which a stream of pressurized air 54 entrains a plurality of liquid particles 56 as the liquid particles 56 exit the ink jet array 26. An absorbent padding 60 can be placed at the bottom of the chamber 52. The absorbent padding 60 operates to collect any liquid particles 56 that are not entrained by the stream of pressurized air 54 inside the chamber 52. In one embodiment of the invention, the absorbent padding 60 is replaceable, allowing the ink jet calibration tool to be cleaned easily and efficiently.

Figure 3:
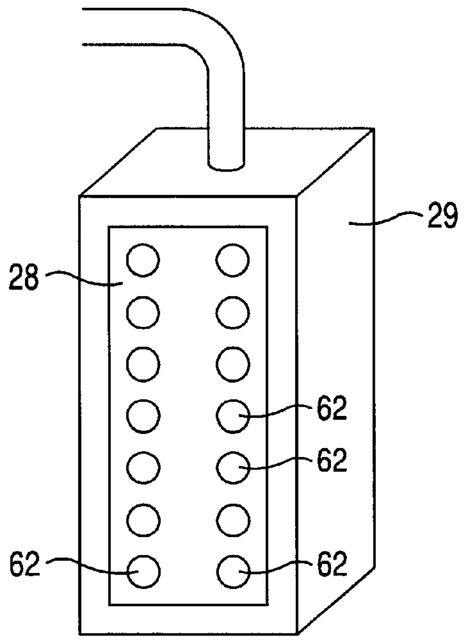
FIG. 3 is a representation of a portion of the thermal ink jet array including one orifice plate.
Figure 4:
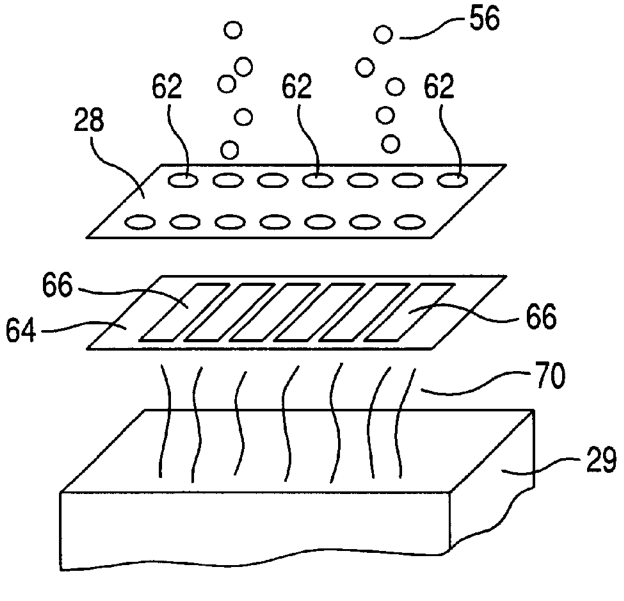
FIG. 4 is an exploded view of the structure surrounding the orifice plate of FIG. 3.

FIGS. 3 and 4 show representations of a single thermal ink jet calibration head 29. The calibration head 29 includes an orifice plate 28. The orifice plate 28 includes a plurality of orifices 62 of equal size. Each individual orifice 62 includes its own nozzle (not shown) from which individual liquid particles 56 will be emitted. In one embodiment of the invention, although the orifices 62 on a particular orifice plate 28 are of the same size, the orifices 62 on one orifice plate 28 are of a size different than the orifices 62 an each of the other orifice plates 28. This arrangement permits the ink jet calibration tool 20 to use particles 56 of different sizes during calibration. In one embodiment of the invention, the calibration head 29 is a standard print head as used on many common ink jet printing systems.

The orifice plate 28 can be coupled to a resistor plate 64 including a plurality of resistors 66. The resistors 66, upon instruction from the control unit 30, operate to vaporize the ink and force it out of the adjacent orifices 62. When the resistors are not heated, ink 70 is not permitted to flow through the orifices 62. This allows a user to regulate the quantities of the particles 56 that are emitted by the array 26. In the event that multiple supplies or varying types of ink or other carriers are coupled to the ink jet calibration tool 20, the control unit 30 can also provide the user with the ability to switch between types of carriers. The control unit 30 can also allow a user to heat the resistors 66 on fewer than all of the resistor plates 64 at one time. Other functions may also be imparted into the control unit depending upon the particular system requirements.

The display panel 32 is capable of displaying a variety of data. One of the important pieces of information that can be displayed by the display panel 32 is the number of particles 56 that have been emitted through the orifices 62 since the beginning of a particular test. Similarly, the rate at which particles 56 are emitted per second, minute, or other time frame could also be displayed. Other information that can be viewed through the display panel 32 includes the size of the particles 56 being emitted, the intervals at which particles 56 are being emitted, that rate at which the liquid carrier is flowing to the array 26, the rate at which the gaseous substance flows into the ink jet calibration tool 20, and the status of the ink jet calibration tool 20 (i.e., whether the system is active, inactive, on or off). The display panel may also indicate whether the ink jet calibration tool needs to be cleaned.

Both the control unit 30 and the display panel 32 are operatively connected to the array 26 so as to permit the user to alter and/or view the individual performance characteristics of the ink jet calibration tool 20.

The control unit 30 allows the user to regulate a number of features of the ink jet calibration tool 20. For example, the control unit enables the user to start and stop the flow of particles 56 to each of the calibration heads 29. This permits the user to select the size of the particles 56 to be emitted from the array 26, to be entrained into the flow of pressurized gas 54, and to enter the particle counter 36. The control unit 30 also provides the user with the ability to alter the rate at which ink 70 flows into the array 26 and through the respective orifice plates 28. Additional features of the control panel 30 can include actuators to start, stop and modify the flow of pressurized gas 54, actuators to activate and deactivate the ink jet calibration tool 20, and actuators to alter the intervals at which individual orifices 62 are opened and closed.

According to one embodiment of the invention, the operation of the ink jet calibration tool 20 is generally as follows. The ink jet calibration tool is coupled to the particle counter 36 in such a manner as to allow the stream of pressurized gas 54 to flow directly from the ink jet calibration tool 20 to the particle counter 36. An external gas source (not shown) is coupled to the ink jet calibration tool 20 via the tubing 38. If the carrier supply 24 is external from the ink jet calibration tool 20, the carrier supply is also coupled to the ink jet calibration tool 20. When a calibration test is to begin, the user activates the source of pressurized gas, resulting in a stream of gas 54 passing through the chamber 52. The user then operates the control unit 30 to input the proper settings. These settings include the size of the particles 56 to be emitted, the rate at which particles 56 are emitted into the chamber, the flow rate of the ink or other carrier 70 and/or the pressurized gas stream 54, etc. All of these settings will be visible to the user on the display panel 32. The user then actuates the control unit 30 to begin the calibration test.

During the calibration test, a regulated flow rate for the ink or other carrier 70 is sent to the array 26 of calibration heads 28. Depending upon the settings input into the control unit 30, only the orifices 62 on one of the orifice plates 28 will be caused to emit ink by the resistors 66. The carrier 70 will then be fired through the open orifices 62 on that particular orifice plate 28 while being blocked from passing through the other orifice plates 28. As the carrier 70 passes through the orifices 62, it will form a plurality and regulated amount of liquid particles 56. Because the key variables such as the flow rate and orifice sizes are known, it is possible to calculate the number of particles 56 that will be formed as the carrier 70 passes through the orifices 62. Standard methods of making this type of calculation are well known in the art.

After the particles 56 exit the orifices 62, they are ejected into the chamber 52. The particles 56 are then entrained into the stream of pressurized gas 54. The stream 54 is pressurized to a high enough level that stream will force substantially all of the particles into the exit tube 34. When combined with the stream 54, the particles 56 form an aerosol mixture as the particles 56 enter the exit tube 34. The individual particles 56 then enter particle counter 36. The particle counter 36, whose function is readily understood by those skilled in the art, then proceeds to count the number, size, and/or rate of the particles 56 that enter the particle counter.

The display unit 32 on the ink jet calibration tool 20 also monitors the number, size, and/or rate of the particles 56 as they exit the array 26. Because the user is capable of observing these statistics for both the calibration tool 20 (on the display panel 32) and the particle counter 36, the user can readily determine whether the statistics from the particle counter 36 are drastically different from the results on the ink jet calibration tool. In the event that the results are different, the user can then have the particle counter 36 repaired and/or replaced.

While the preferred embodiment of the invention as implemented in a prototype system has been described, it will be understood by those skilled in the art to which the invention pertains that numerous modifications and changes may be made without departing from the true spirit and scope of the invention. For example, the type of carrier can vary widely depending upon cost, manufacturing, and performance specifications. Additionally, the types of individual components such as the air filter, display panel, and control unit can vary for several reasons without departing from the invention's broader aspects. The particular arrangement of many of the components both inside and outside the ink jet calibration system can also vary. The present application is therefore accordingly intended to define the scope of the invention precisely in the claims appended to and forming a part of this application.

What is claimed is:

1. A calibration system for a particle counter, comprising:

a chamber;

an air inlet pathway, the inlet pathway providing a gaseous substance to the chamber;

a supply source of a liquid carrier operatively connected to the chamber;

an array of thermal inkjet heads substantially within the chamber for receiving and transmitting the liquid carrier from the supply source, each thermal inkjet head including an plate with a plurality of orifices;

an outlet pathway operatively connected to the chamber; and a controller operatively connected to the array of thermal inkjet heads and the supply source, wherein the liquid carrier is introduced into the gaseous substance as a plurality of liquid particles after exiting the array, and wherein the controller regulates the size of the particles and rate at which the particles exit the array and are entrained by a flow of the gaseous substance.

2. The system of claim 1, wherein the array includes orifices of different sizes.

3. The system of claim 2, wherein the controller regulates the intervals at which particles are transferred through the array.

4. The system of claim 2, wherein the controller is an electronic controller.

5. The system of claim 4, further comprising an interface for displaying the size and number of particles that are transferred through the array.

6. The system of claim 5, further comprising an absorbent padding at the bottom of the chamber, the padding receiving excess carrier fluid that does not form particles.

7. The system of claim 6, wherein the absorbent padding is replaceable.

8. The system of claim 1, further comprising a particle counter coupled to and receiving particles from the outlet pathway.

9. A particle counter calibration system, comprising:

a calibration chamber including:

an air intake portion for transferring a stream of a gaseous substance; and an array of inkjet heads including a plurality of orifices of different sizes;

a supply of a liquid carrier operatively connected to the chamber;

a control unit operatively connected to the array of inkjet heads and the supply of liquid carrier;

wherein the liquid carrier forms a plurality of liquid particles when flowing through the array before being entrained by the stream of a gaseous substance, and wherein the size of the liquid particles and the rate at which particles exit the array are regulated by the control unit.

10. The calibration system of claim 9, wherein the control unit comprises an electronic controller.

11. The calibration system of claim 10, further comprising a display unit, the display unit displaying the number of particles that exit the array during a given time frame.

12. The calibration system of claim 11, further comprising an exit conduit coupled to the chamber, wherein the liquid particles flow through the exit conduit after exiting the array and are entrained by the stream of a gaseous substance.

13. The calibration system of claim 12, wherein the control unit regulates the intervals at which liquid particles are transferred through the array.

14. The calibration system of claim 13, wherein the control unit displays the size of the liquid particles that exit the array.

15. The calibration system of claim 14, further comprising a particle counter operatively connected to the exit conduit, wherein the liquid particles enter the particle counter from the exit conduit.

16. The calibration system of claim 13, wherein the calibration chamber includes a padding for receiving excess amounts of liquid carrier which does not pass through the exit conduit.

17. The calibration system of claim 14, wherein the control unit controls the amount of time before liquid particles begin to exit the array.

18. A system for calibrating a particle counter, comprising:

an inlet passageway for receiving a gaseous material;

a chamber operatively connected to the air inlet passageway and including an array of inkjet heads having orifices of different sizes;

a reservoir for supplying a liquid material to the chamber;

a particle counter operatively connected to the chamber; and means for controlling the number of liquid particles that exit the array, wherein the liquid material passes through the controlling means to form a plurality of liquid particles and is entrained in a flow of the gaseous material, and wherein the controlling means regulates the size of the particles and rate at which the liquid particles are entrained in the flow of the gaseous material.

19. The system of claim 18, further comprising means for displaying the number of particles that exit the controlling means.

20. The system of claim 19, wherein the chamber includes an absorbent padding for absorbing excess liquid material.

21. The system of claim 20, wherein the controlling means comprises and electronic controller.

* * * * *